(12) United States Patent
Matsuura et al.

(10) Patent No.: US 6,786,864 B2
(45) Date of Patent: Sep. 7, 2004

(54) ENDOSCOPIC SYSTEM AND METHOD FOR POSITIONING AN INDWELLING TUBE

(75) Inventors: Nobuyuki Matsuura, Hino (JP); Raifu Matsui, Hino (JP); Toshio Nakamura, Hachioji (JP); Hisao Yabe, Hachioji (JP); Masaaki Nakazawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/067,585

(22) Filed: Feb. 5, 2002

(65) Prior Publication Data

US 2002/0183591 A1 Dec. 5, 2002

(30) Foreign Application Priority Data

Feb. 6, 2001 (JP) .......................................... 2001-029958
Jan. 31, 2002 (JP) .......................................... 2002-023347

(51) Int. Cl.[7] .................................................. A61B 1/00
(52) U.S. Cl. ......................................... 600/104; 600/127
(58) Field of Search ................................. 600/114, 127, 600/129, 153, 175, 104–106; 604/164.13, 523, 528, 533

(56) References Cited

U.S. PATENT DOCUMENTS

| 4,825,259 | A | * | 4/1989 | Berry, Jr. .................. 356/241.4 |
| 4,947,827 | A |   | 8/1990 | Opie et al. |
| 5,257,617 | A | * | 11/1993 | Takahashi .................... 600/123 |
| 5,503,616 | A | * | 4/1996 | Jones .......................... 600/153 |
| 5,630,782 | A | * | 5/1997 | Adair .......................... 600/133 |
| 5,643,175 | A | * | 7/1997 | Adair .......................... 600/133 |
| 5,876,329 | A | * | 3/1999 | Harhen ........................ 600/125 |
| 6,022,313 | A | * | 2/2000 | Ginn et al. .................. 600/114 |
| 6,071,233 | A | * | 6/2000 | Ishikawa et al. ............ 600/104 |
| 6,306,081 | B1 | * | 10/2001 | Ishikawa et al. ............ 600/127 |

\* cited by examiner

*Primary Examiner*—John P. Leubecker
(74) *Attorney, Agent, or Firm*—Scully, Scott, Murphy & Presser (57) ABSTRACT

An endoscope including; a fixing member detachably mounted to a distal end portion of an endoscope insertion part for detachably fixing and holding a distal end portion of an indwelling tube or a distal end portion of a guide member for guiding the indwelling tube, both of which are provided along the axial direction of the insertion part, to the distal end portion of the insertion part.

13 Claims, 7 Drawing Sheets

ENDOSCOPIC SYSTEM AND METHOD FOR POSITIONING AN INDWELLING TUBE

CROSS-REFERENCE TO RELATED APPLICATIONS

This application is based upon and claims the benefit of priority from the prior Japanese Patent Application No. 2001-29958, filed Feb. 6, 2001 and No. 2002-023347 filed on Jan. 31, 2002 in Japan, the entire contents of which are incorporated herein by reference.

BACKGROUND OF THE INVENTION (1) Field of the Invention

This invention relates to an endoscopic system and a method for positioning an indwelling tube. Generally, an endoscope for medical use can be utilized for minor surgery within the body cavity and for obtaining a biopsy.

(2) Description of the Related Art

For example, the endoscope disclosed in U.S. Pat. No. 4,947,827 discloses a biopsy tube assembly outside an insertion part thereof. In Japanese Patent Laid-Open Publication No.11-192203, an outer-mounted channel is attached and fixed to the outside of the insertion part of endoscope. Through the outer-mounted channel, a treating instrument or the like can be inserted into the body cavity.

Conventionally, a guide member such as an indwelling tube and a guide wire protrude past an insertion part through the channel. This enables the guide member, such as the indwelling tube and the guide wire to be navigated into and to indwell in the body cavity.

Therefore, the method for positioning an indwelling tube in the body cavity in the above-mentioned endoscope of the prior art goes through the following procedure.

(i) The insertion part is inserted into the body cavity.

(ii) The guide wire is inserted through the channel.

(iii) The indwelling tube is inserted along the guide wire into the channel.

(iv) The indwelling tube is guided to a targeted position in the body cavity.

(v) The indwelling tube is positioned at the targeted position.

However, the conventional endoscope complicates the operation of the indwelling tube, since each length of guide wire and indwelling tube has to be twice or more than that of the endoscope insertion part in pulling out the endoscope after the indwelling tube is positioned at the targeted position.

Also in the above-mentioned endoscope, it is impossible to insert an indwelling tube having the same or greater diameter than the inner diameter of the channel for treating instruments. Therefore, if an indwelling tube having a larger outer diameter than the inner diameter of the channel for treating instruments is desired, it is necessary to pull out the endoscope insertion part outside the body while the guide wire is kept indwelling and to guide the indwelling tube along the indwelling guide wire to a targeted position in the body cavity. This operation is very complicated. Another problem in this operation is to guide the indwelling tube along the guide wire to a targeted position in the body cavity while the endoscope insertion part is kept pulled out. In other words, this operation cannot be observed and leads to a complicated procedure.

In view of the foregoing, an object of the present invention is to provide an endoscopic system and the method for positioning an indwelling tube whereby operability is improved and indwelling is easily accomplished.

BRIEF SUMMARY OF THE INVENTION

Accordingly, an endoscope is provided. The endoscope comprises a fixing member detachably mounted to a distal end portion of an endoscope insertion part for detachably fixing and holding a distal end portion of an indwelling tube or a distal end portion of a guide member for guiding the indwelling tube, both of which are provided along the axial direction of the insertion part, to the distal end portion of the insertion part.

Also provided is an endoscopic system. The endoscopic system comprises: an endoscope having an elongate insertion part for insertion into the body cavity; and a fixing member mounted to a distal end portion of the insertion part, said fixing member having means for fixedly holding an indwelling tube provided along the axial direction of said insertion part and said fixing member having further means for detachably fixing and holding a distal end portion of a guide member for guiding said indwelling tube to a distal end portion of said insertion part.

Still further provided is a method for positioning an indwelling tube. The method comprises: detachably mounting a guide catheter fixing member to a distal end portion of an elongate insertion part inserted into the body cavity; fixing and holding a distal end portion of a guide catheter along the axial direction of said insertion part, to said guide catheter fixing member; inserting said insertion part into a body cavity for reaching a targeted position, while the distal end portion of said guide catheter is fixedly held; withdrawing the distal end portion of said guide catheter from said guide catheter fixing member; inserting a guide wire into said guide catheter to permit the end of said guide wire to protrude from the distal end of said guide catheter; permitting the end of said guide wire to reach said targeted position, while said guide catheter is pulled out of the body cavity; and inserting said indwelling tube along said guide wire from the outside of the body cavity to said targeted position to position said indwelling tube at said targeted position inside the body cavity; and withdrawing said insertion part out of the body cavity.

Still yet further provided is a fixing member for mounting to a distal end portion of an insertion part of an endoscope. The fixing member comprises: means for fixedly holding an indwelling tube provided along the axial direction of said insertion part and means for detachably fixing and holding a distal end portion of a guide member for guiding said indwelling tube to a distal end portion of said insertion part.

BRIEF DESCRIPTION OF THE SEVERAL VIEWS OF THE DRAWING

These and other features, aspects, and advantages of the apparatus and methods of the present invention will become better understand with regard to the following description, appended claims, and accompanying drawings where:

DETAILED DESCRIPTION

Figure 1:
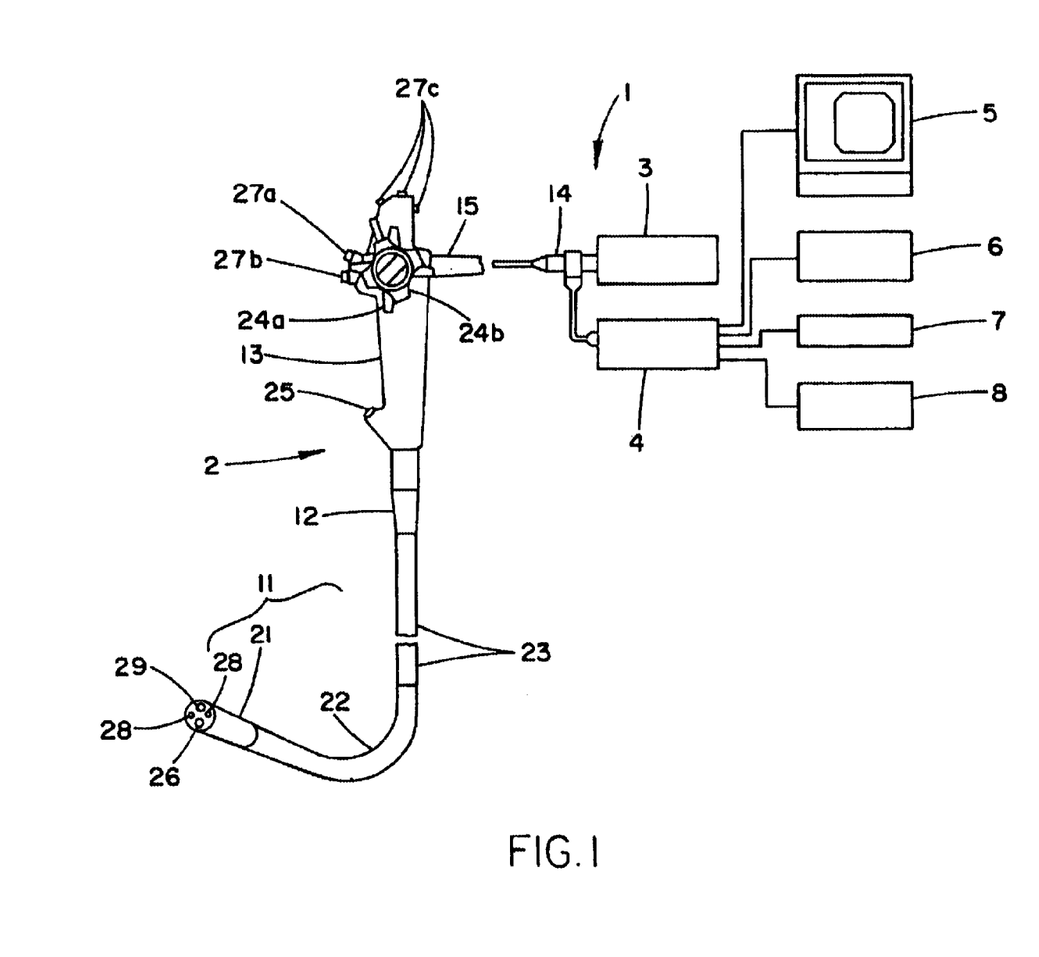
FIG. 1 illustrates a schematic representation of an endoscopic system according to a first embodiment of the present invention.

The embodiments of the present invention are now explained with reference to FIGS. 1 to 12. As shown in FIG. 1, an endoscopic system 1 according to a first embodiment of the present invention mainly comprises an electronic endoscope 2 (hereinafter "endoscope"), a light source apparatus 3, a video processor 4 and a monitor 5.

The endoscope 2 has an imaging means (not shown) on the distal end thereof. The imaging means functions as an imaging device.

The light source apparatus 3 supplies illumination to the endoscope 2. The video processor 4 processes image signals taken by the imaging device of the endoscope 2. The monitor 5 receives the image signals output by the video processor 4 and displays the images observed by the endoscope 2.

In addition, the video processor 4 is connected to a VTR 6 for recording and playing image signals, a video printer 7 for printing an object image by image signals, a video disk 8 as a mass storage device for recording image signals.

The endoscope 2 has an elongate and flexible insertion part 11 which can be inserted into a targeted body cavity, a control section 13 being also used as a holding portion which is connected through a bend stopper 12 to a proximal end of the insertion part 11, and a flexible universal cord 15 which extends from the side of the control section 13 and has a connector section 14 at the end thereof.

The insertion part 11 has a stiff distal end portion 21, a bending section 22 and a flexible portion 23, which are respectively located from the distal end toward the proximal end of the insertion part 11. The bending section 22 can be bent and is continuously formed to the proximal end of the distal end portion 21. The flexible portion 23 is continuously formed to the proximal end of the bending section 22.

The control section 13 is provided with an UP/DOWN bending control knob 24a and a RIGHT/LEFT bending control knob 24b.

The UP/DOWN bending control knob 24a is used to bend the bending section 22 of the insertion part 11 upward and downward by means of a remote operation of the UP/DOWN control knob 24a. The RIGHT/LEFT bending control knob 24b is used to bend the bending section 22 to the right and the left by means of a remote operation of the RIGHT/LEFT control knob 24b. The UP/DOWN control knob 24a and the RIGHT/LEFT control knob 24b can be operated simultaneously for bending the bending section 22 in an oblique direction, not only up and down, and right and left.

An instrument channel port 25 is provided near the front end of the control section 13. The instrument channel port 25 is connected to a channel (not shown) within the insertion part 11 for inserting treating instruments. The channel for inserting treating instruments communicates with an opening 26 in the distal end portion 21. A treating instrument inserted into the instrument channel port 25 is advanced through the channel until it protrudes from the distal end side of the opening 26.

The control section 13 has an air/water valve 27a, a suction valve 27b and a plurality of control switches 27c.

The air/water valve 27a has the function of remotely supplying air/water to the distal end portion 21. The suction valve 27b is used to remotely apply suction to the distal end portion 21. The control switch 27c has the function of remotely operating functions of the video processor 4 such as freezing images, releasing images, changing of light adjustment, and the like.

The light source apparatus 3 supplies light to the endoscope 2. Light supplied by the light source apparatus 3 is transmitted through a light guide (not shown) provided within the endoscope 2, and then through an illumination lens system 28 located at the end of the insertion part 11 for illuminating an object.

An illuminated object image is focused on the imaging means, such as a CCD, through an objective lens system 29 built-in to the distal end portion 21. The video processor 4 processes image signals from the imaging means by a means of signal processing circuit (not shown) and transmits the same to the monitor 5 for display.

Figure 2:
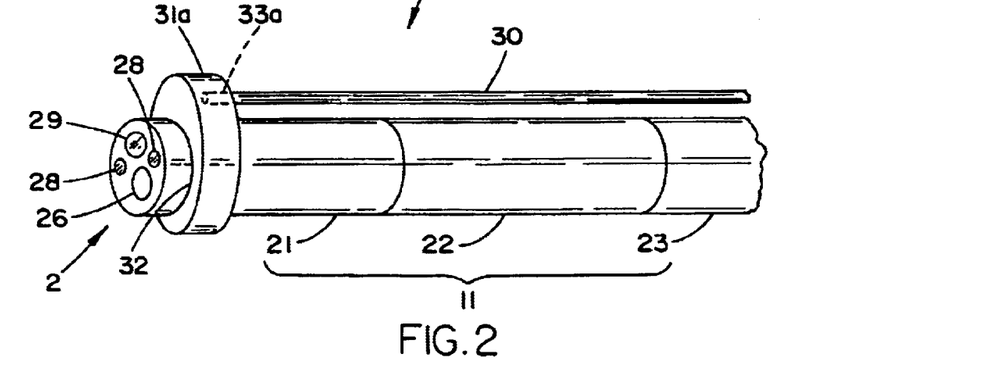
FIG. 2 illustrates a perspective view of a distal end of the endoscope insertion part of FIG. 1.

As shown in FIG. 2, the endoscope 2 can be provided with such guide members as an indwelling tube, a guide wire, or the like along the exterior of the insertion part 11. In FIG. 2, a guide catheter 30 is used as a guide member.

In the endoscopic system according to the first embodiment, the distal end portion of the guide catheter 30 is detachably fixed and held to the side of distal end portion 21. The guide catheter 30 is fixed and held by a fixing member, such as a guide catheter-fixing member 31a that is detachably mounted to the distal end portion 21.

The fixing member 31a is preferably formed of an elastic member and is preferably substantially cylindrical. The fixing member 31a has a through hole 32. The fixing member 31a is detachably mounted to the distal end portion 21 of the endoscope, by passing the outer surface of the distal end portion 21 into the through hole 32.

Figure 3A:
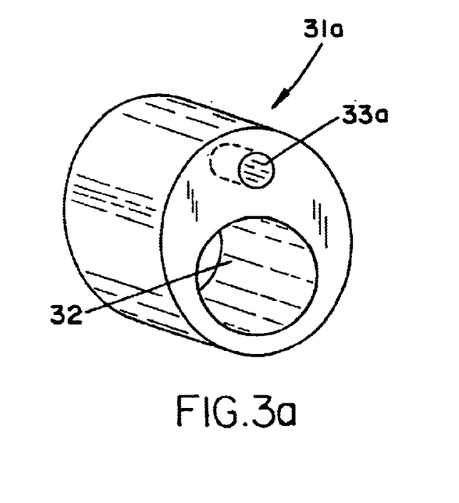
FIGS. 3a and 3b illustrate perspective and sectional views, respectively, of a guide catheter fixing member for attaching to the distal end of the endoscope insertion part of FIG. 2.
Figure 3B:
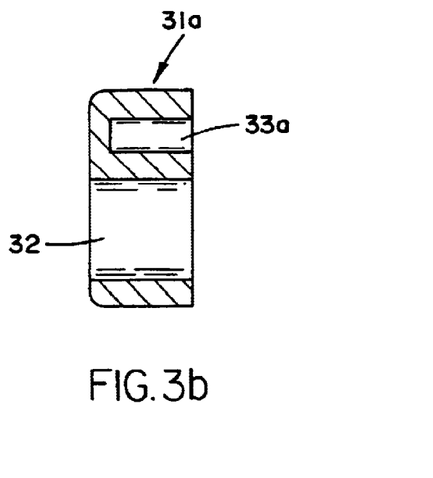

As shown in FIGS. 3a and 3b, the inside diameter of the through hole 32 is preferably formed slightly smaller than the outside diameter of the distal end portion 21, such that the fixing member 31a is tightly fixed to the distal end portion 21 by means of an elastic deformation of the fixing member 31a.

The fixing member 31a has a holding portion, which is preferably a hole 33a and means for fixing and holding the guide catheter 30 in the hole 33a. The inside diameter of the holding portion 33a is preferably formed slightly smaller than the outside diameter of the distal end portion of the guide catheter 30, such that the distal end portion of the guide catheter 30 is fixedly held by means of an elastic deformation of the fixing member 31a.

Figure 4:
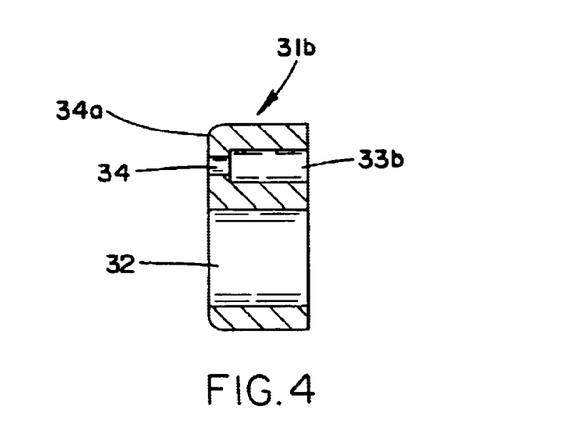
FIG. 4 illustrates a sectional view of an alternative configuration of the guide catheter fixing member.

Instead of the holding portion 33a, a holding portion 33b can be formed in a fixing member 31b as shown in FIG. 4.

The holding portion 33b of the fixing member 31b shown in FIG. 4 has a small diameter portion 34 on the distal end side of the holding portion 33b. The small diameter portion 34 penetrates the fixing member 31b up to a forward end 34a. In the fixing member 31b, before the guide catheter 30 is taken out of the holding portion 33b, a guide wire mentioned later can be inserted into and fixed to the small diameter portion 34.

Figure 6A:
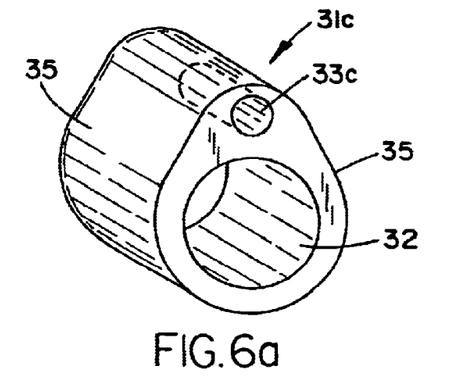
FIGS. 6a–6c illustrate perspective, sectional, and front views, respectively, of a variation of the guide catheter fixing member of FIG. 3.
Figure 6B:
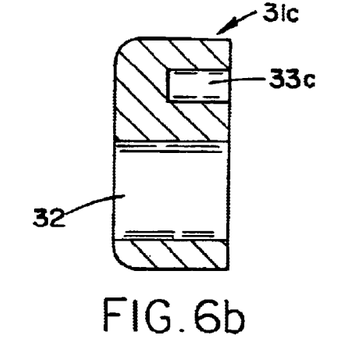
Figure 6C:
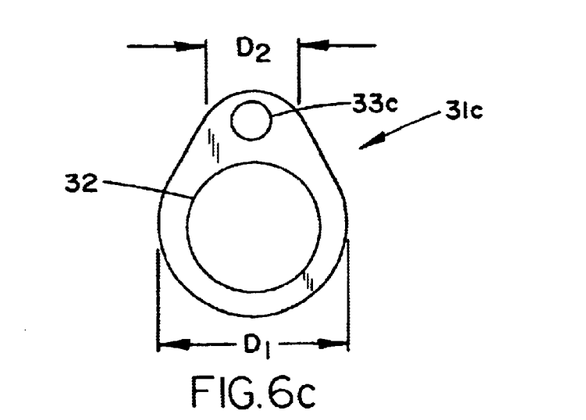

The fixing member may also be formed as shown in FIGS. 6a–6c.

As shown in FIGS. 6a–6c, a fixing member 31c is formed having a teardrop shape wherein the outside diameter D1 on the side of the through hole 32 is larger than the outside diameter D2 on the side of the holding portion 33c. When the fixing member 31c is detachably mounted to the distal end portion 21 of the insertion part 11, the teardrop configuration enables the outside diameter of the distal end portion 21 to be as small as possible for easier insertion.

Figure 7A:
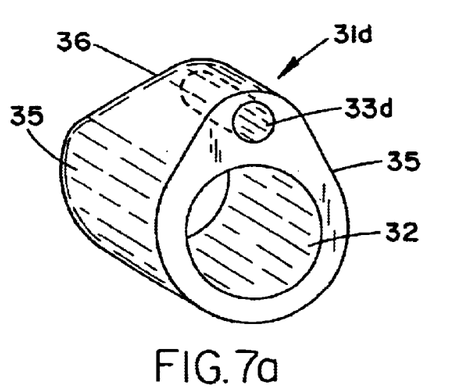
FIGS. 7a and 7b illustrate perspective and sectional views, respectively, of another variation of the guide catheter fixing member of FIG. 6.
Figure 7B:
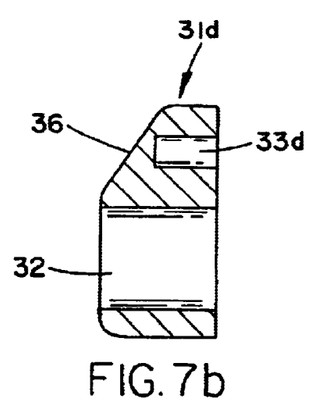

The fixing member may also be formed as shown in FIGS. 7a and 7b.

As shown in FIGS. 7a and 7b, a fixing member 31d is formed having a teardrop shape, similar to the fixing member 31c shown in FIGS. 6a and 6b. Furthermore, a taper 36 is formed on the distal end side of a holding portion 33d. This enables insertion into the body to be much easier, when the fixing member 31d is mounted to the distal end portion 21.

Figure 8A:
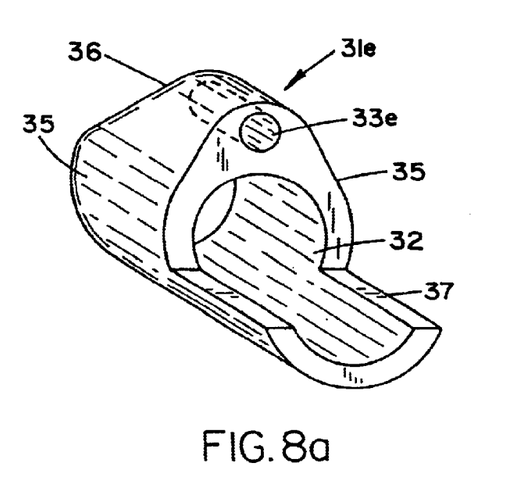
FIGS. 8a and 8b illustrate perspective and sectional views, respectively, of another variation of the guide catheter fixing member of FIG. 7.
Figure 8B:
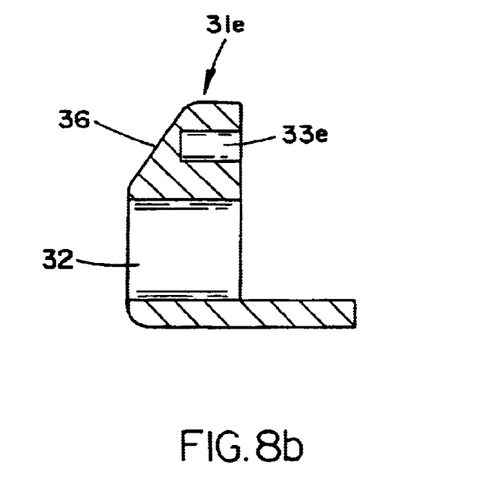

The fixing member may also be formed as shown in FIGS. 8a and 8b.

As shown in FIGS. 8a and 8b, a fixing member 31e is formed having a teardrop shape, similar to the fixing member 31d shown in FIGS. 7a and 7b. An extended portion 37 extending backward is formed at the back end of the fixing member 31e. Due to this configuration, the extended portion 37 of the fixing member 31e can be fixed by a medical tape (not shown) or the like, to thereby attach the fixing member 31e to the distal end portion 21. This fixing by medical tapes or the like enables the fixing member 31e to be fixed more tightly to the distal end portion 21.

Moreover, other means can be used to fix the above-mentioned fixing members 31a–31e, however, the tightly fixing by means of an elastic deformation of the holding portion is preferred. For example, the guide catheter 30 can be fixed and held by the adhesive power of an adherence member that is used as the fixing and holding means.

As mentioned below, the fixing members 31a–31e are inserted with the insertion part 11 into the body cavity, while the guide catheter 30 is kept fixed and held. Preferably, after insertion, by pulling the proximal end portion of the guide catheter 30, the fixing and holding of the distal end portion of the guide catheter 30 is easily released from the fixing member 31a–31e.

The motions of the endoscopic system 1 with the fixing member mounted to the distal end portion 21 will now be explained with reference to FIGS. 5a–5e. Explanation is herein described by example only with reference to the fixing member 31a mounted to the distal end portion 21, however, any of the other fixing members 31b–31e may also be used.

Figure 5A:
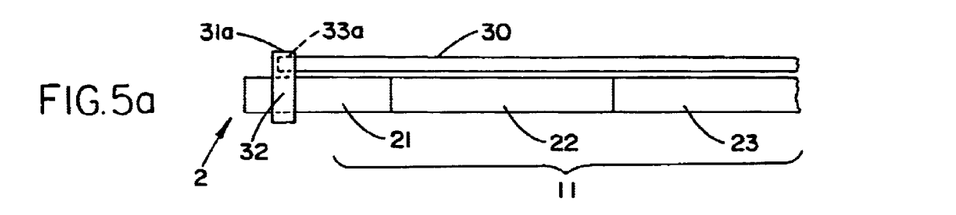
FIGS. 5a to 5e illustrate explanational views showing the method for indwelling the indwelling tube according to a first embodiment of the present invention.

(i) The distal end portion 21 is inserted into the through hole 32 of the fixing member 31a and is fixed to the distal end portion 21.

(ii) The guide catheter 30 is placed along the outer surface of the insertion part 11.

(iii) As shown in FIG. 5a, the distal end portion of the guide catheter 30 is inserted into the holding portion 33a of the fixing member 31a and is fixed to the holding portion 33a.

(iv) The insertion part 11 is inserted into the body cavity, while the distal end portion of the guide catheter 30 remains inserted in the holding portion 33a.

(v) The insertion part 11 is led to a targeted position in the body cavity.

Figure 5B:
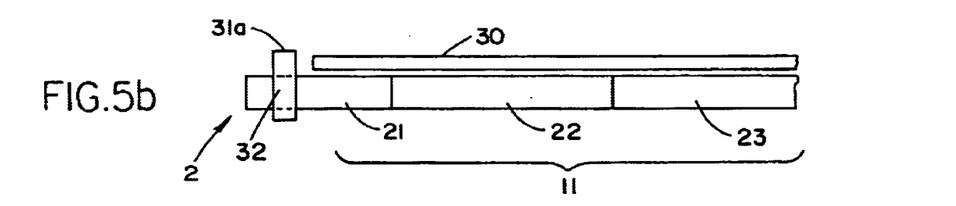

(vi) The proximal end portion of the guide catheter 30 extending outwardly from the body cavity is pulled toward the proximal side. As shown in FIG. 5b, this results in the distal end portion of the guide catheter 30 being withdrawn from the holding portion 33a of the fixing member 31a.

Figure 5C:
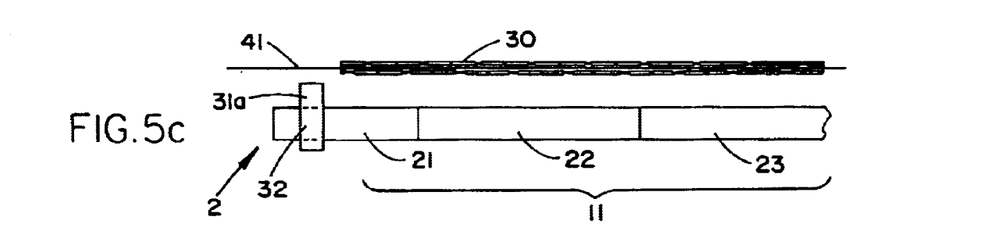

(vii) As shown in FIG. 5c, a guide wire 41 is inserted into the guide catheter 30 and protrudes from the distal end of the guide catheter 30.

Figure 5D:
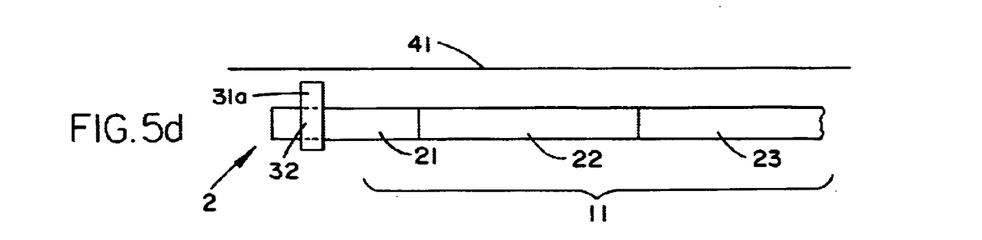

(viii) As shown in FIG. 5d, the guide catheter 30 is pulled out of the body cavity. Simultaneously, the distal end of the guide wire 41 is led to the targeted position.

Figure 5E:
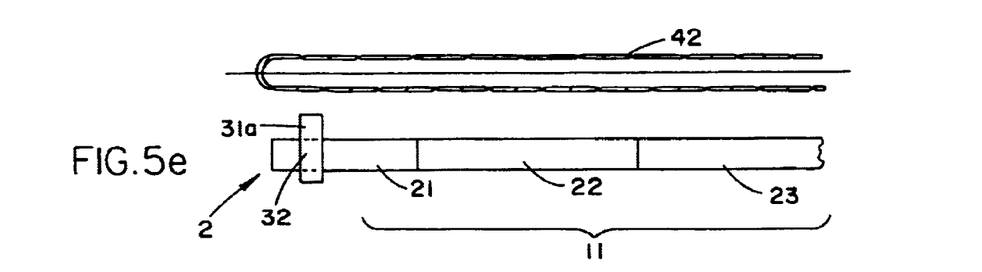

(ix) As shown in FIG. 5e, an indwelling tube 42 is inserted along the guide wire 41 into the body cavity and is led to the targeted position.

(x) The insertion part 11 is pulled out of the body cavity.

The positioning of the indwelling tube 42 is completed by following the above-mentioned steps (i)–(x)

In the above-mentioned steps, the insertion position of the indwelling tube 42 can be confirmed, according to endoscopic images obtained by the endoscope 2.

The above-mentioned indwelling procedure of the indwelling tube 42 brings about the following advantages. Even if the endoscope 2 is not pulled out, the indwelling tube 42 having a larger diameter than the inside diameter of the channel for inserting treating instruments of the endoscope 2 can indwell. This leads to an improvement in the operability of the endoscopic system 1. Moreover, the position of the indwelling tube can be confirmed with endoscopic images, since the endoscope 2 is not pulled out during the steps. Therefore, the indwelling tube 42 can indwell at an exact position.

In the above-mentioned indwelling procedure of the indwelling tube 42, the fixing member may be used for directly fixing and holding the end of the indwelling tube 42 without the guide wire 41 or the guide catheter 30 or the like.

In this embodiment, the present invention is applied to an electronic endoscope in which the distal end portion 21 includes an imaging means (not shown), such as a CCD. However, the present invention is not limited to this type. For example, the present invention may be applied to an optical endoscope in which an illuminated object image is taken by an objective lens system built-in to a distal end portion and the object image is transmitted to an eyepiece by transmitting means such as an image guide fiber bundle. The present invention can also be applied to an endoscope in which an insulation cover is mounted to the distal end portion 21.

An endoscopic system 1 according to a second embodiment of the present invention will now be explained with reference to FIGS. 9–11.

In the above-mentioned first embodiment, the guide catheter 30 is located along the outer surface of the insertion part 11. The fixing member 31a detachably fixes and holds a distal end portion of the guide catheter 30 to a side of the distal end portion 21. The fixing member 31a is detachably mounted to the distal end portion 21.

In the second embodiment, a catheter 50 is located along an outer surface of the insertion part 11. A fixing member 51 detachably fixes and holds the distal end portion of the catheter 50 to the side of the distal end portion 21. The fixing member 51 is detachably mounted to the distal end portion 21. The other structures are the same as those in the first embodiment. Like reference numerals denote like elements and a detail description is omitted, therefore.

Figure 9:
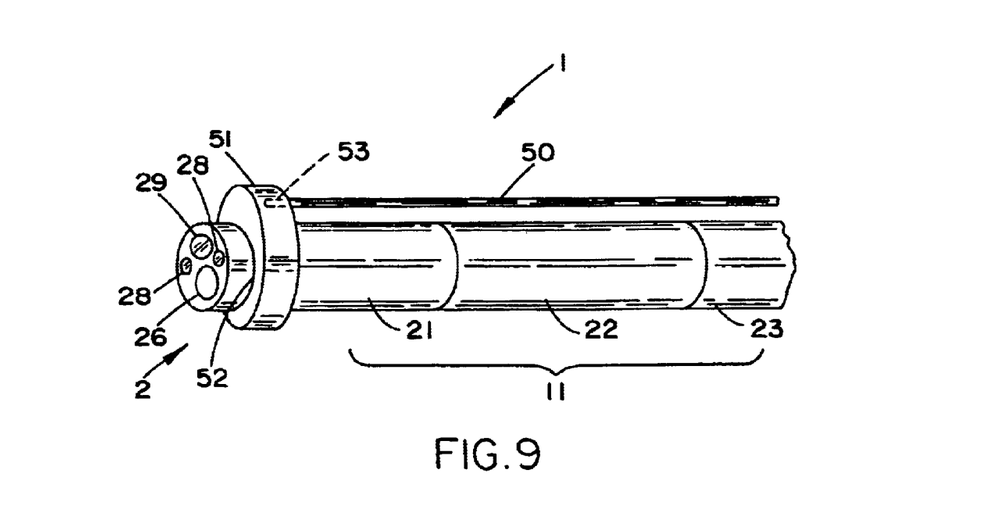
FIG. 9 illustrates a perspective view showing a distal end of an endoscope insertion part according to a second embodiment of the present invention.

As shown in FIG. 9, a catheter 50 is located along the outer surface of the insertion part 11 of the endoscope 2. The fixing member 51 fixes and holds the distal end portion of the catheter 50 thereto and is formed of substantially cylindrical elastic material which is substantially the same as the above-mentioned fixing member 31a. The fixing member 51 has a through hole 52 for detachably mounting the fixing member 51 to the distal end portion 21, by engaging the outer surface of the distal end portion 21.

Figure 10A:
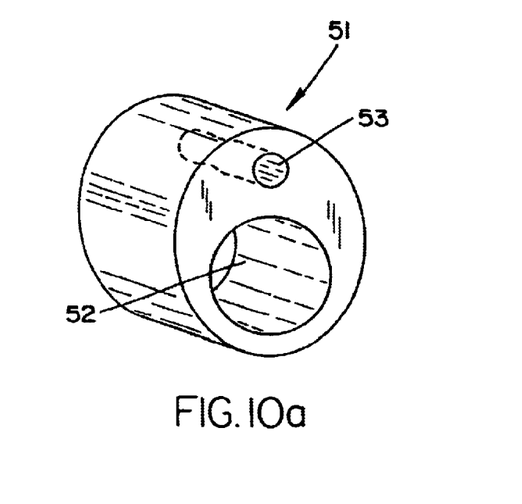
FIGS. 10a and 10b illustrate perspective and sectional views, respectively of a catheter fixing member for mounting to the distal end of the endoscope insertion part of FIG. 9.
Figure 10B:
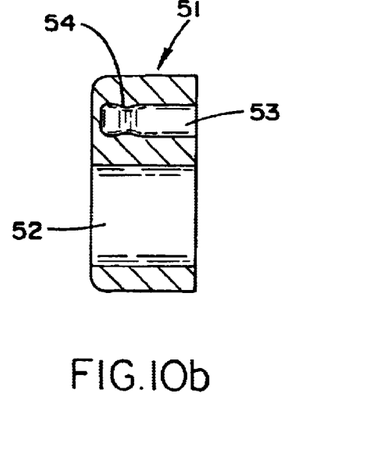
Figure 11:
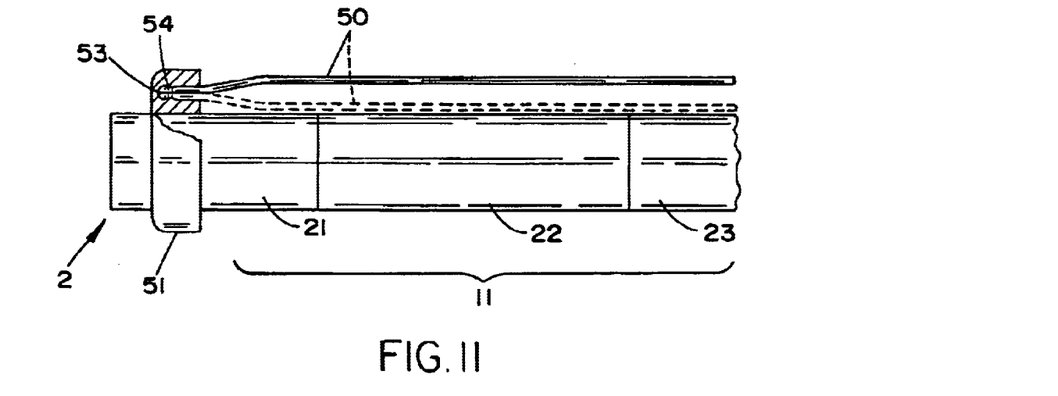
FIG. 11 illustrates a partial sectional view showing a method for positioning an indwelling tube wherein a distal end of an endoscope insertion part is illustrated.

The inside diameter of the through hole 52 shown in FIGS. 10a and 10b is formed slightly smaller than the outside diameter of the distal end portion 21 to thereby tightly fix the fixing member to the distal end portion 21 by means of the elastic deformation of the fixing member 51.

The fixing member 51 has a holding portion, such as a hole 53, for fixing and holding the catheter 50. The inside diameter of the holding portion 53 is formed slightly smaller than the outside diameter of the catheter 50. Furthermore, a neck portion 54 is provided.

The distal end portion of the catheter 50 is inserted into the holding portion 53 and is elastically deformed. Moreover, the distal end portion of the catheter 50 is elastically deformed by the neck portion 54, and fixed and held by the holding portion 53. The structure of the fixing member 51 may be the same as those of the fixing members 31b–31e explained with regard to FIGS. 6–8.

The indwelling procedure of the catheter 50 with the endoscopic system 1 having the fixing member 51 mounted to the distal end portion 21 will now be explained.

(i) The distal end portion 21 is inserted into the through hole 52 of the fixing member 51, and is fixed to the distal end portion 21.
(ii) The catheter 50 is placed along the outer surface of the insertion part 11.
(iii) The distal end portion of the catheter 50 is inserted into the holding portion 53 of the fixing member 51, and is fixed to the holding portion 53.
(iv) The insertion part 11 is inserted into the body cavity.
(v) The insertion part 11 is led to a targeted position in the body cavity.
(vi) The proximal end portion of the catheter 50 extending outwardly from the body cavity is pulled toward the proximal side. This results in the distal end portion of the catheter 50 being dismounted from the holding portion 53 of the fixing member 51. (vii) The distal end of the catheter 50 is led to the targeted position in the body cavity.
(viii) The insertion part 11 is withdrawn from the body cavity.

The indwelling of the catheter 50 is completed by following the above-mentioned steps (i)–(viii).

In the above-mentioned steps, the insertion position of the catheter 50 can be confirmed, according to endoscopic images obtained by the endoscope 2.

In the above-mentioned indwelling of the catheter 50, the catheter 50 can indwell directly, without the guide wire 41. Therefore, the operability of the endoscopic system 1 is improved, compared to that of the guide catheter indwelling in the above-mentioned first embodiment.

A third embodiment of the present invention is explained with reference to FIGS. 12a–12d.

In the third embodiment, an adherence tape is used as a fixing member. The adherence tape detachably fixes and holds the distal end portion of the guide wire 41 to the side of the distal end portion 21. The other structures are the same as those of the above-mentioned first embodiment. Like reference numerals denote like elements and a detail description is omitted, therefore.

As shown in FIGS. 12a–12d, the guide wire 41 is placed along the outer surface of the insertion part 11 of the endoscope 2. An adherence tape 55 such as medical tapes or the like is used as a fixing member to fix and hold the distal end portion of the guide wire 41.

The indwelling method of the guide wire 41 using the adherence tape 55 will now be explained.

Figure 12A:
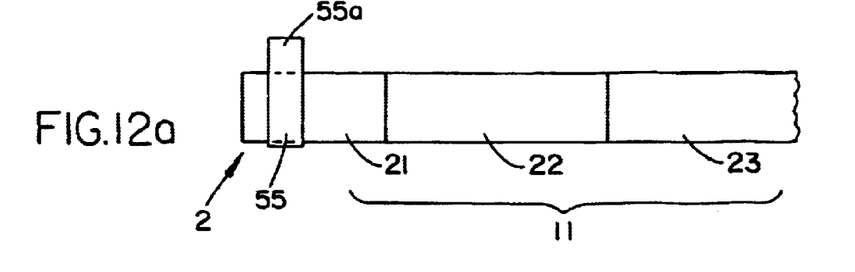
FIGS. 12a to 12d illustrate explanational views showing the method for positioning a guide wire wherein a distal end of an endoscope insertion part is illustrated, according to a third embodiment of the present invention.

(i) As shown in FIG. 12a, the adherence tape 55 is wound around the distal end portion 21. The adherence tape 55 is wound in the counterclockwise direction viewing from the distal end side of the distal end portion 21.

As shown in FIG. 12a, the end of the wound adherence tape 55 is kept loose from the outer surface of the distal end portion 21.

Figure 12B:
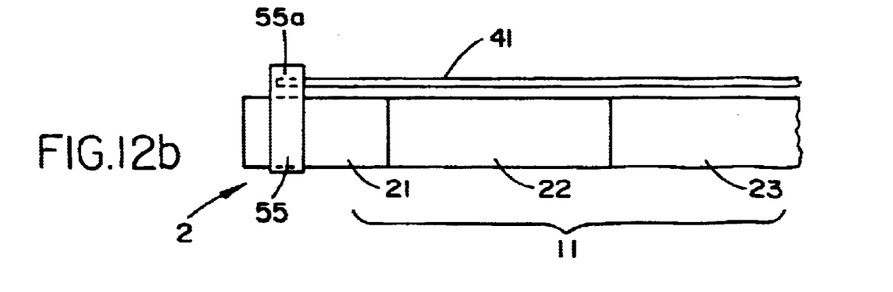
Figure 12C:
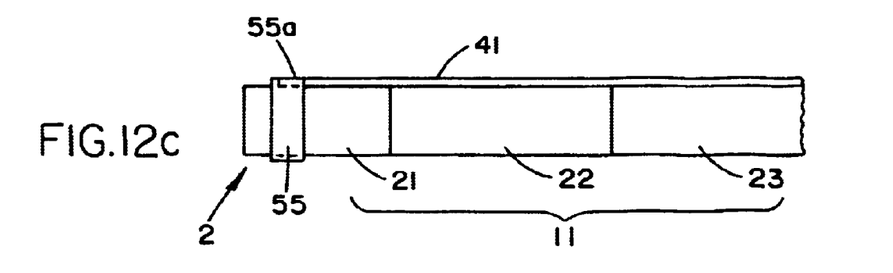
Figure 12D:
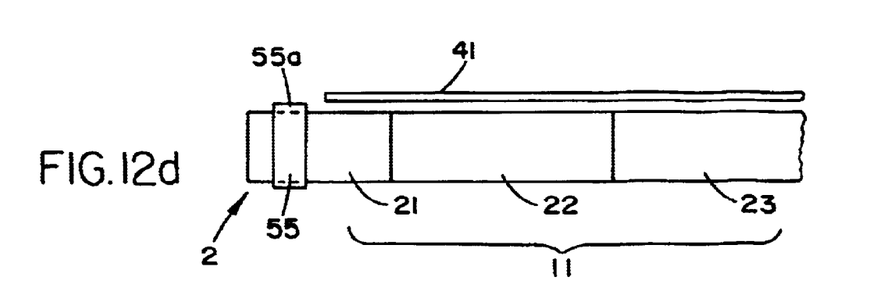

(ii) As shown in FIG. 12b, the distal end portion of the guide wire 41 is adhered to an adherence portion 55a where the adherence tape 55 is loose from the outer surface of the distal end portion 21.
(iii) As shown in FIG. 12c, the end of the adherence tape 55 is turned up for fixing the distal end portion of the guide wire 41. Due to this step, the end of the guide wire 41 is fixed to the distal end portion 21.
(iv) The insertion part 11 is inserted into the body cavity.
(v) The insertion part 11 is led to a targeted position in the body cavity.
(vi) The proximal end portion of the guide wire 41 extending outwardly of the body cavity is pulled toward the proximal side, thereby pulling the distal end portion of the guide wire 41 out from the adherence portion 55a of the adherence tape 55, as shown in FIG. 12d.
(vii) The distal end of the guide wire 41 is led to the targeted position in the body cavity.
(viii) The insertion part 11 is pulled out of the body cavity.

The indwelling of the guide wire 41 is completed by following the above-mentioned steps (i)–(viii).

After these steps, the indwelling tube 42 can be inserted along the guide wire 41 into the body cavity and be led to the targeted position.

In the above-mentioned indwelling of the guide wire 41 in the third embodiment, those skilled in the art will appreciate that a shorter guide wire can be used, compared to the indwelling for the conventional endoscopic system or the above-mentioned first embodiment.

If the guide catheter is inserted into the body cavity in advance and then the guide wire is inserted, the guide wire has to be held on the proximal side (outside the body cavity) so as not to be pulled out together with the guide catheter when pulling out the guide catheter. In order to hold the guide wire on the proximal side, the length of guide wire extending outwardly of the instrument channel port 25 on the proximal side has to be longer than the total length of the guide catheter. Such length of the guide wire complicates the treating the guide wire.

On the other hand, in the endoscopic system of the third embodiment, not only the step of pulling out the guide catheter can be omitted after the insertion of the guide wire, but also the length of guide wire for pulling out the guide catheter can be shortened. Therefore, the operability of the endoscopic system is improved.

Additionally, the endoscope in this embodiment needs no specific fixing member to be mounted to the distal end portion 21, compared to those of the above-mentioned first and second embodiments. The endoscope is therefore more easily inserted into the body cavity. It is possible, moreover, to use an endoscope having a different outside diameter of the distal end portion 21 (,in other words, an endoscope having an outside diameter which does not correspond to the through hole of the fixing member).

As aforementioned, the present invention realizes the simple and easy indwelling of indwelling tube or guide member for guiding the indwelling tube in the body cavity to improve the operability of the same.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An endoscopic system comprising:
   an endoscope including an elongate insertion part for insertion into a body cavity;
   a guide member for guiding an indwelling tube into the body cavity; and
   a fixing member mounted to a distal end portion of the elongated insertion part, at least a distal-most end portion of the guide member being detachably fixed to and held by the fixing member along an axial direction of the endoscope in such a way that the distal-most end portion of the guide member is accommodated within the fixing member.

2. The endoscopic system according to claim 1, wherein said fixing member is formed of an elastic member detachably mounted to the distal end portion by an elastic deformation.

3. The endoscopic system according to claim 2, wherein said elastic member is made from a group consisting of silicon or elastic elastomer.

4. The endoscopic system according to claim 1, wherein said fixing member is formed of an adherence member for adhering to the distal end portion.

5. An endoscopic system comprising:
   an endoscope including an elongated insertion part for insertion into a body cavity;
   an indwelling tube; and
   a fixing member mounted to a distal end portion of the elongated insertion part, at least a distal-most end portion of the indwelling tube being detachably fixed to and held by the fixing member along an axial direction of the endoscope in such a way that the distal-most end portion of the indwelling tube is accommodated within the fixing member.

6. The endoscopic system according to claim 5, wherein said fixing member is formed of an elastic member detachably mounted to the distal end portion by an elastic deformation.

7. The endoscopic system according to claim 6, wherein said elastic member is made from a group consisting of silicon, elastic elastomer.

8. The endoscopic system according to claim 5, wherein said fixing member is formed of an adherence member for adhering to the distal end portion.

9. A method for positioning an indwelling tube comprising:
   detachably mounting a guide catheter fixing member to a distal end portion of an elongate insertion part to be inserted into the body cavity;
   fixing and holding a distal end portion of a guide catheter along the axial direction of said insertion part to said guide catheter fixing member;
   inserting said insertion part into a body cavity to a targeted position, while the distal end portion of said guide catheter is fixedly held;
   withdrawing the distal end portion of said guide catheter from said guide catheter fixing member;
   inserting a guide wire into said guide catheter to permit the end of said guide wire to protrude from the distal end of said guide catheter;
   permitting the end of said guide wire to reach said targeted position, while said guide catheter is pulled out of the body cavity;
   inserting said indwelling tube along said guide wire from the outside of the body cavity to said targeted position to position said indwelling tube at said targeted position inside the body cavity; and
   withdrawing said insertion part out of the body cavity.

10. An endoscopic system comprising:
    an endoscope including an elongate insertion part for insertion into a body cavity;
    a guide member for guiding an indwelling tube into the body cavity; and
    a fixing member detachably mounted to a distal end portion of the endoscope insertion part, at least a distal-most end portion of the guide member being detachably fixed to and held by the fixing member, said fixing member having a holding portion for accommodating at least said distal-most end portion of said guide member.

11. An endoscopic system comprising:
    an endoscope including an elongate insertion part for insertion into a body cavity;
    an indwelling tube; and
    a fixing member detachably mounted to a distal end portion of the elongated insertion part, at least a distal-most end portion of the indwelling tube being detachably fixed to and held by the fixing member, said fixing member having a holding portion for accommodating at least said distal-most end portion of the indwelling tube.

12. An endoscopic system comprising:
    an endoscope including an elongate insertion part for insertion into a body cavity;
    a guide member for guiding an indwelling tube into the body cavity; and
    a fixing member mounted to a distal end portion of the elongated insertion part, at least a distal end portion of the guide member being detachably fixed to and held by the fixing member along an axial direction of the elongated insertion part so that the guide member is to be released from the fixing member by pulling toward a proximal side of the endoscope during insertion.

13. An endoscopic system comprising:

an endoscope including an elongated insertion part for insertion into a body cavity;

an indwelling tube; and a fixing member mounted to a distal end portion of the elongated insertion part, at least a distal end of the indwelling tube being detachably fixed to and held by the fixing member along an axial direction of said elongated insertion part so that the indwelling tube is to be released from the fixing member by pulling toward a proximal side of the endoscope during insertion.

* * * * *